(12) United States Patent
Nifant'ev et al.

(10) Patent No.: US 7,842,764 B2
(45) Date of Patent: Nov. 30, 2010

(54) METALLOCENE COMPOUNDS

(75) Inventors: Ilya Nifant'ev, Moscow (RU); Pavel Ivchenko, Moscow (RU); Yoshikuni Okumura, Kawasaki (JP); Eleonora Ciaccia, Ferrara (IT); Luigi Resconi, Ferrara (IT)

(73) Assignee: Basell Poliolefine Italia s.r.l., Milan (IT)

( * ) Notice: Subject to any disclaimer, the term of this patent is extended or adjusted under 35 U.S.C. 154(b) by 299 days.

(21) Appl. No.: 11/886,646

(22) PCT Filed: Mar. 15, 2006

(86) PCT No.: PCT/EP2006/060767

§ 371 (c)(1),
(2), (4) Date: Sep. 18, 2007

(87) PCT Pub. No.: WO2006/097497

PCT Pub. Date: Sep. 21, 2006

(65) Prior Publication Data

US 2009/0062491 A1 Mar. 5, 2009

(30) Foreign Application Priority Data

Mar. 18, 2005 (EP) ................. 05102189

(51) Int. Cl.
C08F 4/44 (2006.01)

(52) U.S. Cl. ..................................... 526/160

(58) Field of Classification Search ................. 502/152; 526/160
See application file for complete search history.

(56) References Cited

U.S. PATENT DOCUMENTS

| | | | |
|---|---|---|---|
| 4,178,272 A | 12/1979 | Meyer, Jr. et al. | |
| 5,698,487 A | 12/1997 | Sacchetti et al. | |
| 5,770,664 A | 6/1998 | Okumura et al. | |
| 5,770,753 A | 6/1998 | Küber et al. | |
| 5,786,432 A | 7/1998 | Küber et al. | |
| 5,840,644 A | 11/1998 | Küber et al. | |
| 6,051,727 A | 4/2000 | Küber et al. | |
| 6,242,544 B1 | 6/2001 | Küber et al. | |
| 6,255,506 B1 | 7/2001 | Küber et al. | |
| 6,306,996 B1 | 10/2001 | Cecchin et al. | |
| 6,399,533 B2 | 6/2002 | Sacchetti et al. | |
| 6,444,833 B1 | 9/2002 | Ewen et al. | |
| 6,492,539 B1 | 12/2002 | Bingel et al. | |
| 6,559,252 B1 | 5/2003 | Horton et al. | |
| 6,608,224 B2 | 8/2003 | Resconi et al. | |
| 6,635,779 B1 | 10/2003 | Ewen et al. | |
| 6,841,501 B2 | 1/2005 | Resconi et al. | |
| 6,878,786 B2 | 4/2005 | Resconi et al. | |
| 6,949,614 B1 | 9/2005 | Schottek et al. | |
| 6,953,829 B2 | 10/2005 | Kratzer et al. | |
| 6,963,017 B2 | 11/2005 | Bingel et al. | |
| 7,038,070 B2 | 5/2006 | Bingel et al. | |
| 7,053,160 B1 | 5/2006 | Bingel et al. | |
| 7,101,940 B2 | 9/2006 | Schottek et al. | |
| 7,112,638 B2 | 9/2006 | Nifant'ev et al. | |
| 7,141,527 B1 | 11/2006 | Van Baar et al. | |
| 7,141,637 B2 | 11/2006 | Elder et al. | |
| 7,314,903 B2 | 1/2008 | Resconi et al. | |
| 2003/0149199 A1 | 8/2003 | Schottek et al. | |
| 2004/0132612 A1 | 7/2004 | Resconi et al. | |
| 2006/0020096 A1 | 1/2006 | Schottek et al. | |
| 2006/0052553 A1 | 3/2006 | Resconi et al. | |
| 2006/0235173 A1 | 10/2006 | Resconi | |
| 2007/0155919 A1 | 7/2007 | Okumura et al. | |
| 2007/0260023 A1 | 11/2007 | Jones et al. | |
| 2007/0276095 A1 | 11/2007 | Resconi et al. | |

FOREIGN PATENT DOCUMENTS

| | | |
|---|---|---|
| DE | 19917985 | 10/2000 |
| DE | 19962814 | 6/2001 |
| DE | 19962910 | 7/2001 |
| EP | 172961 | 3/1986 |
| EP | 576970 | 1/1994 |
| EP | 633272 | 1/1995 |
| EP | 775707 | 5/1997 |
| GB | 1575894 | 10/1980 |

(Continued)

OTHER PUBLICATIONS

C. Carman et al., "Monomer Sequence Distribution in Ethylene-Propylene Rubber Measured by $^{13}$C NMR. 3. Use of Reaction Probability Model," *Macromolecules*, vol. 10(3), pp. 536-544 (1977).

(Continued)

*Primary Examiner*—Ling-Siu Choi
*Assistant Examiner*—Sonya Wright
(74) *Attorney, Agent, or Firm*—Jarrod N. Raphael; Jonathan L. Schuchardt

(57) ABSTRACT

A bridged metallocene compound of formula (I) wherein: M is an atom of a transition metal; X, is a hydrogen atom, a halogen atom, or a hydrocarbon-based group; R1 is a C1-C40 hydrocarbon radical; R2 and R3, form together a condensed 3-7 membered ring; R4 is a hydrogen atom or a C1-C40 hydrocarbon radical; W is an aromatic 5 or 6 membered ring.

(I)

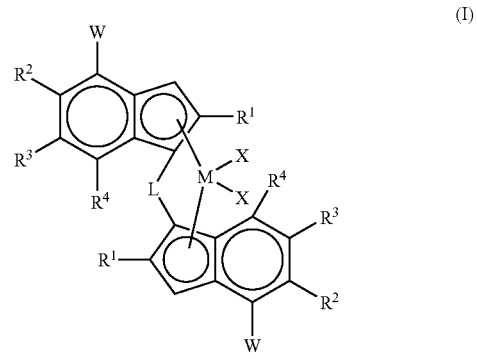

8 Claims, 1 Drawing Sheet

FOREIGN PATENT DOCUMENTS

| | | |
|---|---|---|
| GB | 938491 | 9/1999 |
| JP | 4016851 | 1/1992 |
| JP | 4016853 | 1/1992 |
| JP | 4016854 | 1/1992 |
| JP | 4031868 | 2/1992 |
| WO | 91/02012 | 2/1991 |
| WO | 92/00333 | 1/1992 |
| WO | 95/32995 | 12/1995 |
| WO | 98/40331 | 9/1998 |
| WO | 99/21899 | 5/1999 |
| WO | 99/45043 | 9/1999 |
| WO | 00/31090 | 6/2000 |
| WO | 01/21674 | 3/2001 |
| WO | 01/44318 | 6/2001 |
| WO | 01/47939 | 7/2001 |
| WO | 01/48034 | 7/2001 |
| WO | 01/62764 | 8/2001 |
| WO | 02/102811 | 12/2002 |
| WO | 03/045964 | 6/2003 |
| WO | 03/050761 | 6/2003 |
| WO | 2004/005360 | 1/2004 |
| WO | 2004/050724 | 6/2004 |
| WO | 2004/099269 | 11/2004 |
| WO | 2005/023889 | 3/2005 |
| WO | 2005/058916 | 6/2005 |
| WO | 2005/095468 | 10/2005 |
| WO | 2005/095473 | 10/2005 |
| WO | 2005/095474 | 10/2005 |
| WO | 2005/118654 | 12/2005 |
| WO | 2006/097500 | 9/2006 |
| WO | 2006/100258 | 9/2006 |
| WO | 2006/100269 | 9/2006 |
| WO | 2006/117285 | 11/2006 |
| WO | 2006/120177 | 11/2006 |

OTHER PUBLICATIONS

M. Kakugo et al., "$^{13}$C NMR Determination of Monomer Sequence Distribution in Ethylene-Propylene Copolymers Prepared with δ-TiCl$_3$-Al(C$_2$H$_5$)$_2$Cl," *Macromolecules*, vol. 15(4), pp. 1150-1152 (1982).

A. Rossi et al., "End Groups in 1-Butene Polymerization via Methylaluminoxane and Zirconocene Catalyst," *Macromolecules*, vol. 28(6), pp. 1739-1749 (1995).

N. Naga et al., "Effect of co-catalyst system on α-olefin polymerization with *rac*- and *meso*- [dimethylsilylenebis(2,3,5-trimethyl-cyclopentadienyl)]zirconium dichloride," *Macromol. Rapid. Commun.*, vol. 18, pp. 581-589 (1997).

L. Resconi et al., "C$_1$-Symmetric Heterocyclic Zirconocenes as Catalysts for Propylene Polymerization, 2; *ansa*-Zirconocenes with Linked Dithienocyclopentadienyl-Substituted Indenyl Ligands," *Marcomol. Chem. Phys.*, vol. 206, pp. 1405-1438 (2005).

C. Cobzaru et al., "Novel High and Ultrahigh Molecular Weight Poly(propylene) Plastomers by Asymmetric Hafnocene Catalysts," *Macromol Chem. Phys.*, vol. 206, pp. 1231-1240 (2005).

L. Resconi et al., "Selectivity in Propane Polymerization with Metallocene Catalysts," *Chem. Rev.*, vol. 100(4), pp. 1253-1345 (2000).

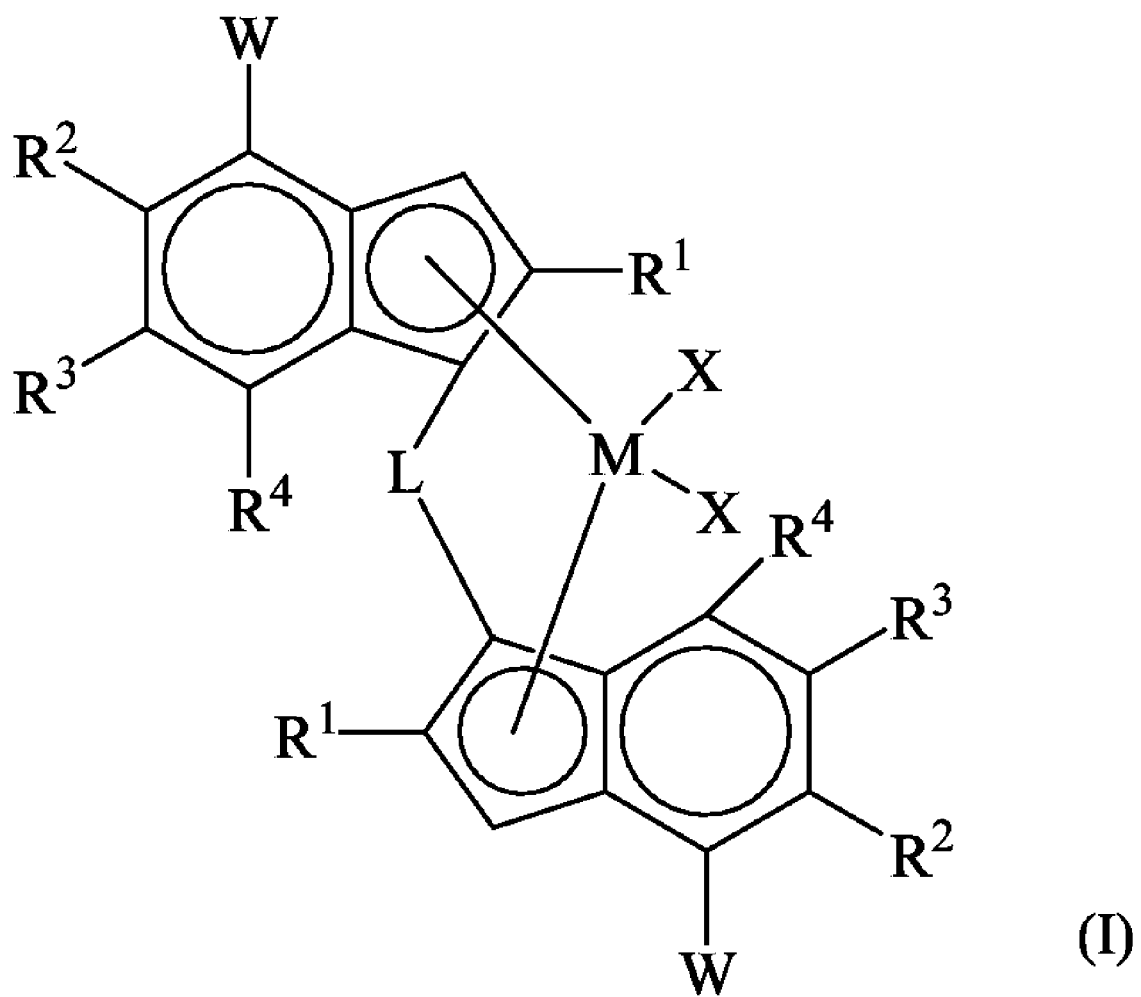
(I)

METALLOCENE COMPOUNDS

The present invention relates to a class of bridged bis indenyl metallocene compounds having $C_2$ symmetry, wherein the indenyl moieties are in particular substituted in position 4 by a phenyl moiety and in positions 5 and 6 by a condensed ring, the present invention further relates to the catalyst system thereof and the polymerization process therefrom. Metallocene compounds are well known in the art as catalyst components for the polymerization of olefins. WO 03/050131 relates to a class of bis indenyl metallocene compounds wherein the indenyl moieties are at least substituted in position 4 and 5. However WO 03/050131 does not report that the substituents on positions 5 and 6 can form a condensed ring. PCT/EP03/12236 relates to a bis indenyl metallocene compound substituted at least in positions 2 5 and 6, wherein the substituents in positions 5 and 6 form a condensed ring. However the substituent in position 4 is defined only in a generic way and in the compounds exemplified in the examples it is always a hydrogen atom. In PCT/EP2004/013827 a class of bis indenyl metallocene compounds wherein the indenyl moieties are substituted in position 5 and 6 by a condensed ring is disclosed. PCT/EP2004/013827 is mainly focused on $C_1$ symmetric structures and there are no explicit disclosures of $C_2$ symmetric compounds. In other words this document is focused on metallocene compounds comprising two cyclopentadienyl moieties having different substitution pattern.

All the compounds disclosed in these documents are able to polymerize alpha-olefins, in particular propylene. However there still is the need to find a new class of metallocene compounds able to polymerize olefin in higher yields and to produce polymers having very high molecular weight.

An object of the present invention is a bridged metallocene compound of formula (I)

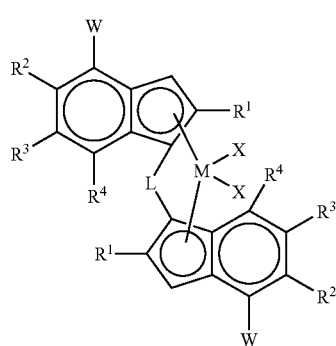

(I)

wherein:

M is an atom of a transition metal selected from those belonging to group 3, 4, or to the lanthanide or actinide groups in the Periodic Table of the Elements; preferably M is zirconium, titanium or hafnium;

X, equal to or different from each other, is a hydrogen atom, a halogen atom, a R, OR, OR'O, $OSO_2CF_3$, OCOR, SR, $NR_2$ or $PR_2$ group wherein R is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical; optionally containing heteroatoms belonging to groups 13-17 of the Periodic Table of the Elements; and R' is a $C_1$-$C_{20}$-alkylidene, $C_6$-$C_{20}$-arylidene, $C_7$-$C_{20}$-alkylarylidene, or $C_7$-$C_{20}$-arylalkylidene radical; preferably X is a hydrogen atom, a halogen atom, a OR'O or R group; more preferably X is chlorine or a methyl radical;

L is a divalent bridging group selected from $C_1$-$C_{20}$ alkylidene, $C_3$-$C_{20}$ cycloalkylidene, $C_6$-$C_{20}$ arylidene, $C_7$-$C_{20}$ alkylarylidene, or a $C_7$-$C_{20}$ arylalkylidene radicals, optionally containing heteroatoms belonging to groups 13-17 of the Periodic Table of the Elements, or it is a silylidene radical containing up to 5 silicon atoms; preferably L is $Si(R^{11})_2$ wherein $R^{11}$ is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical; more preferably L is $Si(CH_3)_2$ or $SiPh_2$;

$R^1$ is a linear $C_1$-$C_{40}$ hydrocarbon radical optionally containing heteroatoms belonging to groups 13-17 of the Periodic Table of the Elements such as methyl or ethyl radical or an alpha branched aryl or arylalkyl radical containing from 2 to 20 carbon atoms optionally containing O, N, S, P and Se atoms, in particular O, N and S atoms such as 2(5-Methiophenyl) or 2(5-Me-furanyl) radicals; preferably $R^1$ is a linear $C_1$-$C_{20}$-alkyl, $C_2$-$C_{40}$ alkenyl, $C_2$-$C_{40}$ alkynyl radical, optionally containing heteroatoms belonging to groups 13-17 of the Periodic Table of the Elements; preferably $R^1$ is a linear $C_1$-$C_{10}$-alkyl radical; more preferably $R^1$ is a methyl, or ethyl radical;

$R^2$ and $R^3$, are part of 4-7 membered ring condensed to the benzene ring of the indenyl moiety; preferably a 5 or 6 membered ring; said ring optionally containing heteroatoms belonging to groups 13-16 of the Periodic Table of the Elements preferably groups 15-16 of the Periodic Table of the Elements; the valence of each atom forming said ring being substituted with $R^{18}$ radicals; that means that is filled with $R^{18}$ groups, wherein $R^{18}$, equal to or different from each other, are hydrogen atoms or a $C_1$-$C_{40}$ hydrocarbon radical; preferably $R^{18}$ is a hydrogen atom or a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical, optionally containing one or more heteroatoms belonging to groups 13-17 of the Periodic Table of the Elements; more preferably $R^{18}$ is a hydrogen atom or a linear or branched, $C_1$-$C_{20}$-alkyl radical; more preferably $R^{18}$ is a hydrogen atom or a methyl or ethyl radical; said ring can be saturated or it can contain double bonds; preferably $R^2$ and $R^3$, form together a condensed saturated 3-7 membered ring;

$R^4$ is a hydrogen atom or a $C_1$-$C_{40}$ hydrocarbon radical optionally containing heteroatoms belonging to groups 13-17 of the Periodic Table of the Elements; preferably $R^4$ is a hydrogen atom or a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical optionally containing heteroatoms belonging to groups 13-17 of the Periodic Table of the Elements; preferably $R^4$ is a hydrogen atom a $C_1$-$C_{10}$-alkyl or a $C_6$-$C_{40}$-aryl radical;

W is an aromatic 5 or 6 membered ring that can contain heteroatoms belonging to groups 15-16 of the Periodic Table of the Elements; the valence of each atom of said ring is substituted with hydrogen atom or it can optionally be substituted with $R^5$ groups, wherein $R^5$, equal to or different from each other, are $C_1$-$C_{40}$ hydrocarbon radicals optionally containing heteroatoms belonging to groups 13-17 of the Periodic Table of the Elements; preferably $R^5$, are linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals optionally containing heteroatoms belonging to groups 13-17 of the Periodic Table of the Elements;

Preferably W is selected from the group comprising the following moieties of formula (Wa), (Wb) and (Wc):

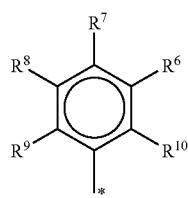 (Wa)

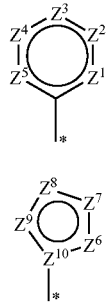 (Wb)

 (Wc)

wherein the * represents the point in which the moiety bounds the indenyl moiety of the compound of formula (I);

$R^6$, $R^7$, $R^8$, $R^9$ and $R^{10}$, equal to or different from each other, are hydrogen atoms or $C_1$-$C_{40}$ hydrocarbon radicals optionally containing heteroatoms belonging to groups 13-17 of the Periodic Table of the Elements; preferably $R^6$, $R^7$, $R^8$, $R^9$ and $R^{10}$, are hydrogen atoms or linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals optionally containing heteroatoms belonging to groups 13-17 of the Periodic Table of the Elements;

$Z^1$ is a nitrogen atom or a $CR^{10}$ group; $Z^2$ is a nitrogen atom or a $CR^6$ group; $Z^3$ is a nitrogen atom or a $CR^7$ group; $Z^4$ is a nitrogen atom or a $CR^8$ group; $Z^5$ is a nitrogen atom or a $CR^9$ group; provided that not more that 2 groups among $Z^1$, $Z^2$, $Z^3$, $Z^4$ and $Z^5$ are nitrogen atoms, preferably not more that one group among $Z^1$, $Z^2$, $Z^3$, $Z^4$ and $Z^5$ is a nitrogen atom;

$Z^6$ is an oxygen atom, a sulfur atom, a $NR^{13}$ group or a $CR^{13}$ group; $Z^7$ is an oxygen atom, a sulfur atom, a $NR^{14}$ group or a $CR^{14}$ group; $Z^8$ is an oxygen atom, a sulfur atom, a $NR^{15}$ group or a $CR^{15}$ group; $Z^9$ is an oxygen atom, a sulfur atom, a $NR^{16}$ group or a $CR^{16}$ group;

$Z^{10}$ is a nitrogen atom or a carbon atom that bonds the indenyl moiety of the structure of formula (I); with the proviso that not more than 1 group among $Z^6$, $Z^7$, $Z^8$, $Z^9$ or $Z^{10}$ is a sulfur atom, an oxygen atom or a nitrogen-containing group atom selected from $NR^{13}$, $NR^{14}$, $NR^{15}$, $NR^{16}$, and a nitrogen atom;

$R^{13}$, $R^{14}$, $R^{15}$ and $R^{16}$, equal to or different from each other, are hydrogen atoms or $C_1$-$C_{40}$ hydrocarbon radicals optionally containing heteroatoms belonging to groups 13-17 of the Periodic Table of the Elements; preferably $R^6$, $R^7$, $R^8$, $R^9$ and $R^{10}$, are hydrogen atoms or linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals optionally containing heteroatoms belonging to groups 13-17 of the Periodic Table of the Elements; more preferably $R^6$, $R^7$, $R^8$, $R^9$ and $R^{10}$ are hydrogen atoms, $C_1$-$C_{40}$-alkyl or $C_6$-$C_{40}$-aryl radicals;

In the moiety of formula (Wa), in a preferred embodiment, $R^7$ is a $C_1$-$C_{40}$-alkyl radical, preferably a branched $C_1$-$C_{40}$-alkyl radical such as a tertbutyl radical, more preferably $R^7$ is a branched $C_1$-$C_{40}$-alkyl radical wherein the carbon atom in position alpha is a tertiary carbon atom and $R^6$, $R^8$, $R^9$ and $R^{10}$ are hydrogen atoms;

In a further preferred embodiment $R^{10}$ and $R^8$ are $C_1$-$C_{40}$-alkyl radicals, preferably they are linear $C_1$-$C_{40}$ alkyl radicals such as methyl radicals and $R^7$, $R^8$ and $R^9$ are hydrogen radicals;

In a further preferred embodiment $R^6$, $R^7$ and $R^8$ are linear or branched $C_1$-$C_{40}$-alkyl radicals such as methyl or tertbutyl radicals and $R^{10}$ and $R^9$ are hydrogen atoms.

In a further preferred embodiment $R^6$, $R^7$, $R^8$, $R^9$ and $R^{10}$ are hydrogen atoms;

In the moiety of formula (Wb), in a preferred embodiment, $Z^1$ is a nitrogen atom and $Z^2$, $Z^3$, $Z^4$ and $Z^5$ are respectively $CR^6$, $CR^7$, $CR^8$ and $CR^9$ wherein the meaning of $R^6$, $R^7$, $R^8$, and $R^9$ is described above; in a further preferred embodiment $Z^3$ is a nitrogen atom and $Z^1$, $Z^2$, $Z^4$ and $Z^5$ are respectively $CR^{10}$, $CR^6$, $CR^8$ and $CR^9$ wherein the meaning of $R^{10}$, $R^6$, $R^8$, and $R^9$ is described above; in a further preferred embodiment $Z^2$ is a nitrogen atom and $Z^1$, $Z^3$, $Z^4$ and $Z^5$ are respectively $CR^{10}$, $CR^7$, $CR^8$ and $CR^9$ wherein the meaning of $R^{10}$, $R^7$, $R^8$, and $R^9$ is described above;

In the moiety of formula (Wc) in a preferred embodiment $Z^6$ is an oxygen atom, a sulfur atom, a $NR^{16}$ group; preferably it is a sulfur atom or a $NR^{16}$; wherein $R^{16}$ is preferably a $C_1$-$C_{40}$-alkyl radical; more preferably $Z^6$ is a sulfur atom; and $Z^7$, $Z^8$, $Z^9$ and $Z^{10}$ are respectively a $CR^{14}$, $CR^{15}$, $CR^{16}$ and a carbon atom, wherein $R^{14}$ is a hydrogen atom or a $C_1$-$C_{40}$-alkyl radical such as methyl or ethyl; and $R^{15}$ and $R^{16}$ are hydrogen atoms or $C_1$-$C_{40}$-alkyl radicals.

Examples of compounds having formula (I) are as follows

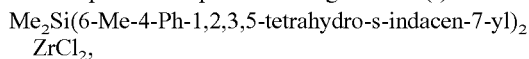

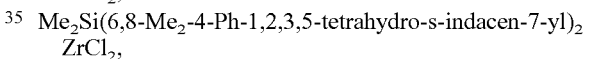

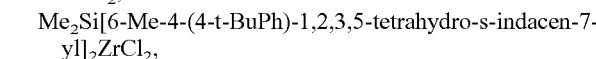

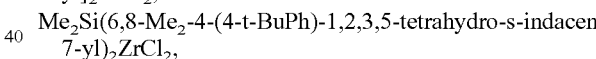

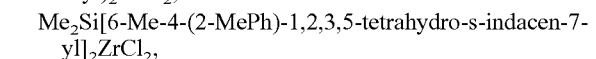

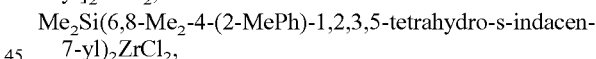

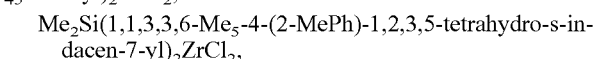

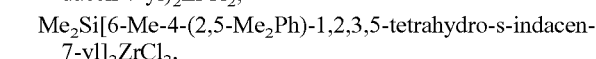

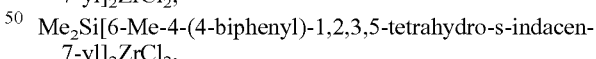

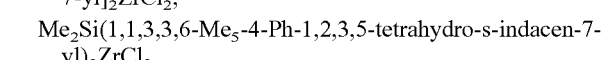

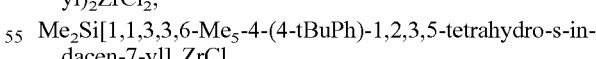

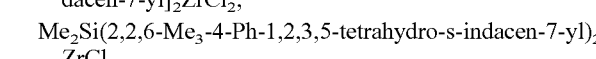

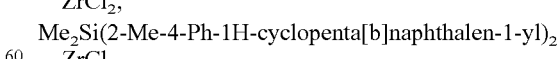

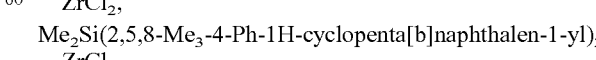

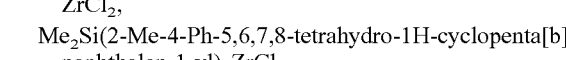

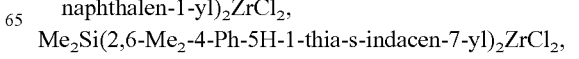

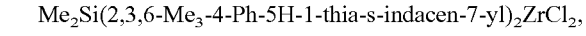

Me$_2$Si(2,6-Me$_2$-4-(4-t-BuPh)-5H-1-thia-s-indacen-7-yl)$_2$ZrCl$_2$,

Me$_2$Si(2,3,6-Me$_3$-4-(4-t-BuPh)-5H-1-thia-s-indacen-7-yl)$_2$ZrCl$_2$,

Me$_2$Si(2-Me-4-Ph-1,5,6,7,8,9-hexahydrocyclohepta[f]inden-1-yl)$_2$ZrCl$_2$,

Me$_2$Si(6-Me-4-(2-benzothiophenyl)-1,2,3,5-tetrahydro-s-indacen-7-yl)$_2$ZrCl$_2$, Me$_2$Si(6-Me-4-(2-(5-methylthiophenyl))-1,2,3,5-tetrahydro-s-indacen-7-yl)$_2$ZrCl$_2$, Me$_2$Si(6-Me-4-(2-(5-methylfuryl))-1,2,3,5-tetrahydro-s-indacen-7-yl)$_2$ZrCl$_2$, Me$_2$Si(6-Me-4-(4-pyridyl)-1,2,3,5-tetrahydro-s-indacen-7-yl)$_2$ZrCl$_2$, and they correspondent dimethyl derivatives.

A preferred class of the compounds of formula (I) is represented by formula (II):

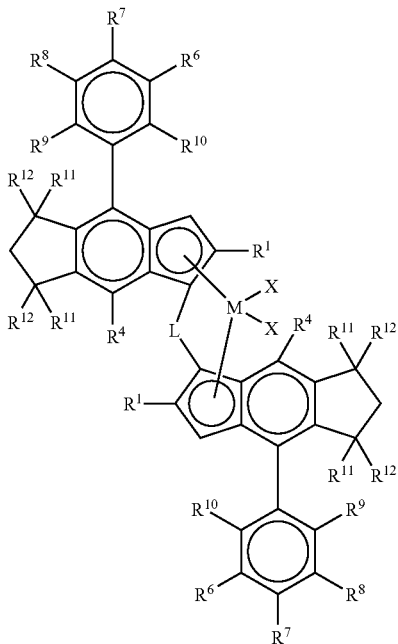

(II)

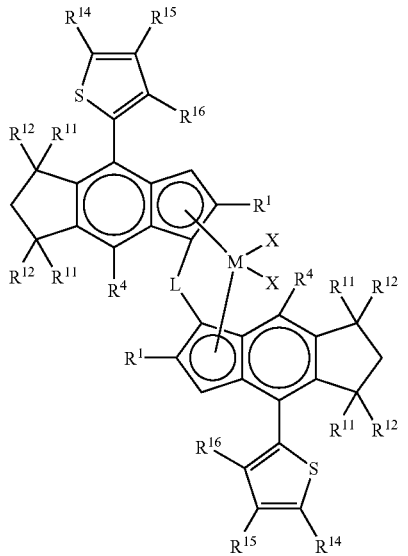

(IIa)

Wherein M, L, X, R$^1$, R$^4$, R$^6$, R$^7$, R$^8$, R$^9$ and R$^{10}$ have the meaning reported above and R$^{11}$ and R$^{12}$, equal to or different from each other, are hydrogen atoms or C$_1$-C$_{40}$ hydrocarbon radicals optionally containing heteroatoms belonging to groups 13-17 of the Periodic Table of the Elements; preferably R$^{11}$ and R$^{12}$ are hydrogen atoms or linear or branched, cyclic or acyclic, C$_1$-C$_{40}$-alkyl, C$_2$-C$_{40}$ alkenyl, C$_2$-C$_{40}$ alkynyl radicals, optionally containing heteroatoms belonging to groups 13-17 of the Periodic Table of the Elements; more preferably R$^{11}$ and R$^{12}$ are hydrogen atoms or C$_1$-C$_{10}$-alkyl radicals such as methyl or ethyl radicals.

A further preferred class of compounds of formula (I) has formula (IIa)

Wherein M, L, X, R$^1$, R$^4$, R$^{11}$, R$^{12}$, R$^{14}$, R$^{15}$ and R$^{16}$ have the meaning reported above.

In the metallocene compounds object of the present invention the two cyclopentadienyl moieties have the same substitution patterns That means that the two indenyl moieties bounded on the central metal atom are substituted in the same way, or in other words, the substituents R$^1$, R$^2$, R$^3$, R$^4$ and W are the same on each indenyl moiety. Preferably the metallocene compounds of formula (I) have C$_2$ symmetry. Metallocene symmetry classes can be found on Resconi et al. Chemical Reviews, 2000, Vol. 100, No. 4 1263 and references herein cited.

Preferably the metallocene compounds object of the present invention are in their racemic (rac) form.

A further object of the present invention is a catalyst system for the polymerization of olefin obtainable by contacting:
a) a metallocene compound of formula (I);
b) at least an alumoxane or a compound able to form an alkylmetallocene cation; and
c) optionally an organo aluminum compound.

Preferably the metallocene compounds have formula (II) or (IIa).

Alumoxanes used as component b) in the catalyst system according to the present invention can be obtained by reacting water with an organo-aluminium compound of formula H$_j$AlU$_{3-j}$ or H$_j$Al$_2$U$_{6-j}$, where the U substituents, same or different, are hydrogen atoms, halogen atoms, C$_1$-C$_{20}$-alkyl, C$_3$-C$_{20}$-cyclalkyl, C$_6$-C$_{20}$-aryl, C$_7$-C$_{20}$-alkylaryl or C$_7$-C$_{20}$-arylalkyl radicals, optionally containing silicon or germanium atoms, with the proviso that at least one U is different from halogen, and j ranges from 0 to 1, being also a non-integer number. In this reaction the molar ratio of Al/water is preferably comprised between 1:1 and 100:1.

The alumoxanes used in the catalyst system according to the invention are considered to be linear, branched or cyclic compounds containing at least one group of the type:

wherein the substituents U, same or different, are defined above.

In particular, alumoxanes of the formula:

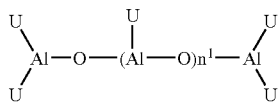

can be used in the case of linear compounds, wherein $n^1$ is 0 or an integer of from 1 to 40 and the substituents U are defined as above; or alumoxanes of the formula:

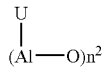

can be used in the case of cyclic compounds, wherein $n^2$ is an integer from 2 to 40 and the U substituents are defined as above.

Examples of alumoxanes suitable for use according to the present invention are methylalumoxane (MAO), tetra-(isobutyl)alumoxane (TIBAO), tetra-(2,4,4-trimethylpentyl)alumoxane (TIOAO), tetra-(2,3-dimethylbutyl)alumoxane (TDMBAO) and tetra-(2,3,3-trimethylbutyl)alumoxane (TTMBAO).

Particularly interesting cocatalysts are those described in WO 99/21899 and in WO01/21674 in which the alkyl and aryl groups have specific branched patterns.

Non-limiting examples of aluminium compounds that can be reacted with water to give suitable alumoxanes (b), described in WO 99/21899 and WO01/21674, are: tris(2,3,3-trimethyl-butyl)aluminium, tris(2,3-dimethyl-hexyl)aluminium, tris(2,3-dimethyl-butyl)aluminium, tris(2,3-dimethyl-pentyl)aluminium, tris(2,3-dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl)aluminium, tris(2-ethyl-3-methyl-pentyl)aluminium, tris(2,3-diethyl-pentyl)aluminium, tris(2-propyl-3-methyl-butyl)aluminium, tris(2-isopropyl-3-methyl-butyl)aluminium, tris(2-isobutyl-3-methyl-pentyl)aluminium, tris(2,3,3-trimethyl-pentyl)aluminium, tris(2,3,3-trimethyl-hexyl)aluminium, tris(2-ethyl-3,3-dimethyl-butyl)aluminium, tris(2-ethyl-3,3-dimethyl-pentyl)aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl)aluminium, tris(2,3-dimethyl-3-phenyl-butyl)aluminium, tris(2-phenyl-propyl)aluminium, tris[2-(4-fluoro-phenyl)-propyl]aluminium, tris[2-(4-chloro-phenyl)-propyl]aluminium, tris[2-(3-isopropyl-phenyl)-propyl]aluminium, tris(2-phenyl-butyl)aluminium, tris(3-methyl-2-phenyl-butyl)aluminium, tris(2-phenyl-pentyl)aluminium, tris[2-(pentafluorophenyl)-propyl]aluminium, tris[2,2-diphenyl-ethyl]aluminium and tris[2-phenyl-2-methyl-propyl]aluminium, as well as the corresponding compounds wherein one of the hydrocarbyl groups is replaced with a hydrogen atom, and those wherein one or two of the hydrocarbyl groups are replaced with an isobutyl group.

Amongst the above aluminium compounds, trimethylaluminium (TMA), triisobutylaluminium (TIBA), tris(2,4,4-trimethyl-pentyl)aluminium (TIOA), tris(2,3-dimethylbutyl) aluminium (TDMBA) and tris(2,3,3-trimethylbutyl) aluminium (TTMBA) are preferred.

Non-limiting examples of compounds able to form an alkylmetallocene cation are compounds of formula $D^+E^-$, wherein $D^+$ is a Brønsted acid, able to donate a proton and to react irreversibly with a substituent X of the metallocene of formula (I) and $E^-$ is a compatible anion, which is able to stabilize the active catalytic species originating from the reaction of the two compounds, and which is sufficiently labile to be removed by an olefinic monomer. Preferably, the anion $E^-$ comprises one or more boron atoms. More preferably, the anion $E^-$ is an anion of the formula $BAr_4^{(-)}$, wherein the substituents Ar which can be identical or different are aryl radicals such as phenyl, pentafluorophenyl or bis(trifluoromethyl)phenyl. Tetrakis-pentafluorophenyl borate is particularly preferred compound, as described in WO 91/02012. Moreover, compounds of formula $BAr_3$ can be conveniently used. Compounds of this type are described, for example, in the International patent application WO 92/00333. Other examples of compounds able to form an alkylmetallocene cation are compounds of formula $BAr_3P$ wherein P is a substituted or unsubstituted pyrrol radical. These compounds are described in WO01/62764. Compounds containing boron atoms can be conveniently supported according to the description of DE-A-19962814 and DE-A-19962910. All these compounds containing boron atoms can be used in a molar ratio between boron and the metal of the metallocene comprised between about 1:1 and about 10:1; preferably 1:1 and 2.1; more preferably about 1:1.

Non limiting examples of compounds of formula $D^+E^-$ are:
Triethylammoniumtetra(phenyl)borate,
Tributylammoniumtetra(phenyl)borate,
Trimethylammoniumtetra(tolyl)borate,
Tributylammoniumtetra(tolyl)borate,
Tributylammoniumtetra(pentafluorophenyl)borate,
Tributylammoniumtetra(pentafluorophenyl)aluminate,
Tripropylammoniumtetra(dimethylphenyl)borate,
Tributylammoniumtetra(trifluoromethylphenyl)borate,
Tributylammoniumtetra(4-fluorophenyl)borate,
N,N-Dimethylbenzylammonium-tetrakispentafluorophenylborate,
N,N-Dimethylhexylamonium-tetrakispentafluorophenylborate,
N,N-Dimethylaniliniumtetra(phenyl)borate,
N,N-Diethylaniliniumtetra(phenyl)borate,
N,N-Dimethylaniliniumtetrakis(pentafluorophenyl)borate,
N,N-Dimethylaniliniumtetrakis(pentafluorophenyl)aluminate,
N,N-Dimethylbenzylammonium-tetrakispentafluorophenylborate,
N,N-Dimethylhexylamonium-tetrakispentafluorophenylborate,
Di(propyl)ammoniumtetrakis(pentafluorophenyl)borate,
Di(cyclohexyl)ammoniumtetrakis(pentafluorophenyl)borate,
Triphenylphosphoniumtetrakis(phenyl)borate,
Triethylphosphoniumtetrakis(phenyl)borate,
Diphenylphosphoniumtetrakis(phenyl)borate,
Tri(methylphenyl)phosphoniumtetrakis(phenyl)borate,
Tri(dimethylphenyl)phosphoniumtetrakis(phenyl)borate,
Triphenylcarbeniumtetrakis(pentafluorophenyl)borate, Triphenylcarbeniumtetrakis(pentafluorophenyl)aluminate,
Triphenylcarbeniumtetrakis(phenyl)aluminate,
Ferroceniumtetrakis(pentafluorophenyl)borate,
Ferroceniumtetrakis(pentafluorophenyl)aluminate.
Triphenylcarbeniumtetrakis(pentafluorophenyl)borate, and
N,N-Dimethylaniliniumtetrakis(pentafluorophenyl)borate.

Organic aluminum compounds used as compound c) are those of formula $H_jAU_{3-j}$ or $H_jAl_2U_{6-j}$ as described above.

The catalysts of the present invention can also be supported on an inert carrier. This is achieved by depositing the metallocene compound a) or the product of the reaction thereof with the component b), or the component b) and then the metallocene compound a) on an inert support. The support can be a porous solid such as talc, a sheet silicate, an inorganic oxide or a finely divided polymer powder (e.g. polyolefin). Suitable inorganic oxides may be found among the oxides of elements of groups 2, 3, 4, 5, 13, 14, 15 and 16 of the Periodic Table of the Elements. Examples of oxides preferred as supports include silicon dioxide, aluminum oxide, and also mixed oxides of the elements calcium, aluminum, silicon, magnesium or titanium and also corresponding oxide mixtures, magnesium halides, styrene/divinylbenzene copolymers, polyethylene or polypropylene. Other inorganic oxides which can be used alone or in combination with the abovementioned preferred oxidic supports are, for example, MgO, $ZrO_2$, $TiO_2$ or $B_2O_3$.

A suitable class of supports which can be used is that constituted by porous organic supports functionalized with groups having active hydrogen atoms. Particularly suitable are those in which the organic support is a partially crosslinked styrene polymer. Supports of this type are described in European application EP-633 272.

Another class of inert supports particularly suitable for use according to the invention is that of polyolefin porous prepolymers, particularly polyethylene.

A further suitable class of inert supports for use according to the invention is that of porous magnesium halides such as those described in International application WO 95/32995.

The support materials used preferably have a specific surface area in the range from 10 to 1 000 $m^2$/g, a pore volume in the range from 0.1 to 5 ml/g and a mean particle size of from 1 to 500 μm. Preference is given to supports having a specific surface area in the range from 50 to 500 $m^2$/g, a pore volume in the range from 0.5 to 3.5 ml/g and a mean particle size in the range from 5 to 350 μm. Particular preference is given to supports having a specific surface area in the range from 200 to 400 $m^2$/g, a pore volume in the range from 0.8 to 3.0 ml/g and a mean particle size of from 10 to 100 μm.

The inorganic support can be subjected to a thermal treatment, e.g. to remove adsorbed water. Such a drying treatment is generally carried out at from 80 to 300° C., preferably from 100 to 200° C., with drying at from 100 to 200° C. preferably being carried out under reduced pressure and/or a blanket of inert gas (e.g. nitrogen), or the inorganic support can be calcined at from 200 to 1000° C. to produce the desired structure of the solid and/or set the desired OH concentration on the surface. The support can also be treated chemically using customary desiccants such as metal alkyls, preferably aluminum alkyls, chlorosilanes or $SiCl_4$, or else methylaluminoxane. Appropriate treatment methods are described, for example, in WO 00/31090.

The inorganic support material can also be chemically modified. For example, treatment of silica gel with $(NH_4)_2SiF_6$ leads to fluorination of the silica gel surface, or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and are preferably likewise freed of adhering moisture, solvent residues or other impurities by means of appropriate purification and drying operations before use. It is also possible to use functionalized polymer supports, e.g. supports based on polystyrene, via whose functional groups, for example ammonium or hydroxy groups, at least one of the catalyst components can be immobilized. The solid compound obtained by supporting the catalyst system object of the present invention on a carrier in combination with the further addition of the alkylaluminium compound either as such or prereacted with water if necessary, can be usefully employed in the gas-phase or slurry polymerization.

Therefore a further object of the present invention is a catalyst system as described above, further comprising d) an inert carrier.

The catalyst system comprising the metallocene compound of formula (I) can be used for polymerizing olefins, in particular alpha-olefins in high yields to obtain polymers having high molecular weight. Therefore a further object of the present invention is a process for preparing a alpha-olefin polymer comprising contacting under polymerization conditions one or more alpha-olefins of formula $CH_2=CHA$ wherein A is hydrogen or a $C_1$-$C_{20}$ alkyl radical, in the presence of a catalyst system as described above.

Non limitative examples of alpha-olefins of formula $CH_2=CHA$ are: ethylene, propylene, 1-butene, 1-hexene, 1-octene and 4-methyl-1-pentene, preferred alpha olefins are ethylene propylene and 1-butene.

The metallocene compounds of formula (I) object of the present invention are particularly suitable for the homo and copolymerization of propylene. In fact, the metallocene-based catalyst system of the present invention when used for homo or copolymerizing propylene are able to give polymers having a high molecular weight in high yields also at high temperatures rendering thus possible to use it in the industrial plants that use polymerization temperatures higher than 50° C. and that can be comprised between 60 and 120° C.

As said above the metallocene compounds of formula (I) are particularly suitable for the copolymerization of propylene, therefore a further object of the present invention is a process for the preparation of propylene copolymers comprising the step of contacting, under polymerization conditions, propylene with ethylene or one or more alpha olefins of formula $CH_2=CHA^1$, wherein $A^1$ is a $C_2$-$C_{20}$ alkyl radical, in the presence of a catalyst system described above.

Examples of alpha olefins of formula $CH_2=CHA^1$ are 1-butene, 1-hexene, 1-octene and 4-methyl-1-pentene, preferred alpha olefins are ethylene and 1-butene; more preferred alpha olefin is ethylene.

The content of alpha-olefins derived units in the propylene copolymer object of the present invention ranges from 0.1 to 90% by mol; preferably it ranges from 5% by mol to 70% by mol; more preferably it ranges from 10% by mol to 60% by mol.

The metallocene compounds of the present invention are also particularly suitable for the preparation of copolymers of ethylene and higher alpha olefins, such as propylene, 1-butene, 1-hexene, 1-octene. The copolymers have a comonomer content ranging from 5 to 50% by mol. Particularly preferred are ethylene/1-butene copolymer having a content of 1-butene derive units ranging from 5 to 50% by mol. Said copolymers can be obtained in high yields by using a gas phase process such a fluidized bed or stirred bed reactor.

The process for the polymerization of olefins according to the invention can be carried out in slurry or in the gas phase.

The hydrocarbon solvent can either be aromatic such as toluene, or aliphatic such as propane, hexane, heptane, or isobutane.

The polymerization temperature is generally comprised between −100° C. and +200° C. and, particularly between 10° C. and +100° C. The polymerization pressure is generally comprised between 0.5 and 100 bar.

The lower the polymerization temperature, the higher are the resulting molecular weights of the polymers obtained.

The polymerization yields depend on the purity of the metallocene compound. The metallocene compounds obtained by the process of the invention can therefore be used as such or can be subjected to purification treatments.

When the metallocene compounds of the present invention are used as catalyst component in a polymerization process the activity of the catalyst system is strongly activated by the presence of hydrogen. This feature is even more important if it is considered that the molecular weight of the obtained polymer is not influenced in a considerable way by this addiction and it remains quite high for industrial use even in the presence of high amount of hydrogen. Thus a further object of the present invention is a process for preparing a alpha-olefin polymer comprising contacting under polymerization conditions one or more alpha-olefins of formula $CH_2=CHA$ wherein A is hydrogen or a $C_1$-$C_{20}$ alkyl radical, in the presence of a catalyst system as described above wherein the polymerization reaction I scarried out in the presence of hydrogen. Preferably the amount of hydrogen ranges from 0.5 NL (normal liter) to 10 NL; even more preferably it ranges from 4.5 NL to 8 NL.

In view of the optimum behavior of the metallocene compounds of formula (I) when used for the homo and copolymerization of propylene, the catalyst system based on the metallocene compounds object of the present invention can be used in a multistage process for preparing heterophasic propylene copolymers. Therefore a further object of the present invention is a multistage polymerization process comprising the following steps:

a) polymerizing propylene with optionally ethylene or one or more alpha olefins of formula $CH_2=CHA^1$, wherein $A^1$ is a $C_2$-$C_{20}$ alkyl radical, in the presence of a catalysts system described above;

b) contacting, under polymerization conditions, propylene with ethylene or one or more alpha olefins of formula $CH_2=CHA^1$, and optionally with a non-conjugated diene, in the presence of the polymer obtained in step a) and optionally in the presence of an additional organo aluminum compound;

provided that the polymer produced in step a) is different from the copolymer produced in step b) for the comonomer derived units amount or comonomer derived units structure; wherein the amount of the polymer obtained in step a) ranges from 2% to 98% by weight of the polymer obtained in the whole process and the amount of polymer obtained in step b) ranges from 98% to 2% by weight of the polymer obtained in the whole process. Preferably step a) further comprises a prepolymerization step a-1).

The prepolymerization step a-1) can be carried out by contacting the catalyst system described above with one or more alpha olefins of formula $CH^2=CHA$ wherein A is hydrogen or a $C_1$-$C_{20}$ alkyl radical; preferably said alpha olefin is propylene or ethylene, at a temperature ranging from −20° C. to 70° C., in order to obtain a prepolymerized catalyst system containing preferably from 5 to 500 g of polymer per gram of catalyst system. Step a) of the present invention can be carried out in liquid phase, in which the polymerization medium can be an inert hydrocarbon solvent or the polymerization medium can be liquid propylene optionally in the presence of an inert hydrocarbon solvent, and of ethylene or one or more comonomer of formula $CH_2=CHA^1$, or step a) can be carried out in a gas phase. Said hydrocarbon solvent can be either aromatic (such as toluene) or aliphatic (such as propane, hexane, heptane, isobutane, cyclohexane and 2,2,4-trimethylpentane). Preferably the polymerization medium is liquid propylene. It can optionally contains minor amounts (up to 20% by weight, preferably up to 10% by weight, more preferably up to 5% by weight) of an inert hydrocarbon solvent or of ethylene or one or more comonomer of formula $CH_2=CHA^1$.

Step a) can be carried out in the presence of hydrogen. The amount of hydrogen present during the polymerization reaction is preferably more than 1 ppm; more preferably from 5 to 2000 ppm; even more preferably from 6 to 500 ppm with respect to the propylene present in the reactor. Hydrogen can be added either at the beginning of the polymerization reaction or it can also be added at a later stage after a prepolymerization step has been carried out.

The propylene polymer obtained in step a) is a propylene homopolymer or a propylene copolymer containing up to 20% by mol preferably from 0.1 to 10% by mol, more preferably from 1% to 5% by mol of derived units of ethylene or one or more alpha olefins of formula $CH_2=CHA^1$. Preferred comonomers are ethylene or 1-butene. Preferably in step a) a propylene homopolymer is produced.

The content of the polymer obtained in step a) preferably ranges from 5% to 90% by weight of the polymer produced in the whole process, more preferably it ranges from 10% to 70% by weight and still more preferably from 25% to 65% by weight of the total polymer produced in the whole process.

Step b) can be carried out in liquid phase, in which the polymerization medium can be an inert hydrocarbon solvent or the polymerization medium can be liquid propylene optionally in the presence of an inert hydrocarbon solvent, and of ethylene or one or more comonomer of formula $CH_2=CHA^1$, or step a) can be carried out in a gas phase. Preferably step b) is carried out in a gas phase, preferably in a fluidized or stirred bed reactor. The polymerization temperature is generally comprised between −100° C. and +200° C., and, preferably, between 10° C. and +90° C. The polymerization pressure is generally comprised between 0.5 and 100 bar.

In step b) a propylene copolymer containing from 5% to 90% by mol, preferably from 10% to 50% by mol, more preferably from 15% to 30% by mol of derived units of ethylene or one or more alpha olefins of formula $CH_2=CHA^1$ is produced. Examples of comonomer of formula $CH_2=CHA^1$ that can be used in step b) of the present invention are: 1-butene, 1-pentene, 4-methyl-1-pentene, 1-hexene, 1-octene, 4,6-dimethyl-1-heptene, 1-decene, 1-dodecene, 1-tetradecene, 1-hexadecene, 1-octadecene and 1-eicosene. Preferred comonomers are ethylene or 1-butene.

The content of polymer obtained in step b) preferably ranges from 10 to 95% by weight of the polymer produced in the whole process, preferably it ranges from 30% to 90% by weight and more preferably from 35% to 75% by weight.

The polymer obtained in step b) can optionally contains up to 20% by mol of a non conjugated diene. Non conjugated dienes can be a straight chain, branched chain or cyclic hydrocarbon diene having from 6 to 20 carbon atoms. Examples of suitable non-conjugated dienes are:

straight chain acyclic dienes, such as 1,4-hexadiene and 1,6-octadiene;

branched chain acyclic dienes, such as 5-methyl-1,4-hexadiene, 3,7-dimethyl-1,6-octadiene, 3,7-dimethyl-1,7-octadiene and mixed isomers of dihydro myricene and dihydroocinene;

single ring alicyclic dienes, such as 1,3-cyclopentadiene, 1,4-cyclohexadiene, 1,5-cyclooctadiene and 1,5-cyclododecadiene;

multi-ring alicyclic fused and bridged ring dienes, such as tetrahydroindene, methyl tetrahydroindene, dicyclopentadiene, bicyclo-(2,2,1)-hepta-2,5-diene; and alkenyl, alkylidene, cycloalkenyl and cycloalkylidene norbornenes, such as 5-methylene-2-norbornene (MNB), 5-propenyl-2-norbornene, 5-isopropylidene-2-norbornene, 5-(4-cyclopentenyl)-2-norbornene, 5-cyclohexylidene-2-norbornene, 5-vinyl-2-norbornene and norbornadiene.

Preferred dienes are 1,4-hexadiene (HD), 5-ethylidene-2-norbornene (ENB), 5-vinylidene-2-norbornene (VNB), 5-methylene-2-norbornene (MNB) and dicyclopentadiene (DCPD). Particularly preferred dienes are 5-ethylidene-2-norbornene (ENB) and 1,4-hexadiene (HD).

When present the non-conjugated dienes are preferably incorporated into the polymer in an amount from 0.1% to about 20% by mol, preferably from 0.5% to 15% by mol, and more preferably from 0.5% to 7% by mol. If desired, more than one diene may be incorporated simultaneously, for example HD and ENB, with total diene incorporation within the limits specified above.

A further multistage polymerization process comprises the following steps:

a1) polymerizing propylene with optionally ethylene or one or more monomers selected from alpha olefins of formula $CH_2=CHA^1$, wherein $A^1$ is a $C_2$-$C_{20}$ alkyl radical, in the presence of a catalysts system described above;

b1) contacting, under polymerization conditions, ethylene with propylene or one or more alpha olefins of formula $CH_2=CHA^1$, and optionally with a non-conjugated diene, in the presence of the polymer obtained in step a) and optionally in the presence of an additional organo aluminum compound;

provided that the polymer produced in step a1) is different from the copolymer produced in step b1) for the comonomer derived units amount or comonomer derived units structure;

wherein the amount of the polymer obtained in step a1) ranges from 2% to 98% by weight of the polymer obtained in the whole process and the amount of polymer obtained in step b1) is ranges from 98% to 2% by weight of the polymer obtained in the whole process.

Preferably step a1) further comprises a prepolymerization step a1-1).

The prepolymerization step a1-1) can be carried out by contacting the catalyst system described above with one or more alpha olefins of formula $CH^2=CHA$ wherein A is hydrogen or a $C_1$-$C_{20}$ alkyl radical; preferably said alpha olefin is propylene or ethylene, at a temperature ranging from −20° C. to 70° C., in order to obtain a prepolymerized catalyst system containing preferably from 5 to 500 g of polymer per gram of catalyst system. Step a1) can be carried out in liquid phase, in which the polymerization medium can be an inert hydrocarbon solvent or the polymerization medium can be liquid propylene optionally in the presence of an inert hydrocarbon solvent, and ethylene or one or more comonomer of formula $CH_2=CHA^1$, or step a1) can be carried out in a gas phase. Said hydrocarbon solvent can be either aromatic (such as toluene) or aliphatic (such as propane, hexane, heptane, isobutane, cyclohexane and 2,2,4-trimethylpentane).

Preferably the polymerization medium is liquid propylene. It can optionally contains minor amounts (up to 20% by weight, preferably up to 10% by weight, more preferably up to 5% by weight) of an inert hydrocarbon solvent or of ethylene or one or more comonomer of formula $CH_2=CHA^1$.

Step a1) can be carried out in the presence of hydrogen. The amount of hydrogen present during the polymerization reaction is preferably more than 1 ppm; more preferably from 5 to 2000 ppm; even more preferably from 6 to 500 ppm with respect to the propylene present in the reactor. Hydrogen can be added either at the beginning of the polymerization reaction or it can also be added at a later stage after a prepolymerization step has been carried out.

The propylene polymer obtained in step a1) is a propylene homopolymer or a propylene copolymer containing up to 20% by mol preferably from 0.1 to 10% by mol, more preferably from 1% to 5% by mol of derived units of ethylene or one or more alpha olefins of formula $CH_2=CHA^1$. Preferred comonomers are ethylene or 1-butene. Preferably in step a1) a propylene homopolymer is produced.

The content of the polymer obtained in step a1) preferably ranges from 5% to 90% by weight of the polymer produced in the whole process, more preferably it ranges from 10% to 70% by weight and still more preferably from 25% to 65% by weight of the total polymer produced in the whole process.

Step b1) can be carried out in liquid phase, in which the polymerization medium can be an inert hydrocarbon solvent or the polymerization medium can be a liquid monomer such as ethylene, propylene or one or more comonomer of formula $CH_2=CHA^1$ optionally in the presence of an inert hydrocarbon solvent, or step b1) can be carried out in a gas phase. Preferably step b1) is carried out in a gas phase, preferably in a fluidized or stirred bed reactor. The polymerization temperature is generally comprised between −100° C. and +200° C., and, preferably, between 10° C. and +90° C. The polymerization pressure is generally comprised between 0.5 and 100 bar.

In step b1) an ethylene copolymer containing from 5% to 90% by mol, preferably from 10% to 50% by mol, more preferably from 15% to 30% by mol of derived units of propylene or one or more alpha olefins of formula $CH_2=CHA^1$ is produced. Examples of comonomer of formula $CH_2=CHA^1$ that can be used in step b1) of the present invention are: 1-butene, 1-pentene, 4-methyl-1-pentene, 1-hexene, 1-octene, 4,6-dimethyl-1-heptene, 1-decene, 1-dodecene, 1-tetradecene, 1-hexadecene, 1-octadecene and 1-eicosene. Preferred comonomers are propylene or 1-butene.

The content of polymer obtained in step b1) preferably ranges from 10 to 95% by weight of the polymer produced in the whole process, preferably it ranges from 30% to 90% by weight and more preferably from 35% to 75% by weight.

The polymer obtained in step b1) can optionally contains up to 20% by mol of a non conjugated diene. Non conjugated dienes can be a straight chain, branched chain or cyclic hydrocarbon diene having from 6 to 20 carbon atoms. Examples of suitable non-conjugated dienes are:

straight chain acyclic dienes, such as 1,4-hexadiene and 1,6-octadiene;

branched chain acyclic dienes, such as 5-methyl-1,4-hexadiene, 3,7-dimethyl-1,6-octadiene, 3,7-dimethyl-1,7-octadiene and mixed isomers of dihydro myricene and dihydroocinene;

single ring alicyclic dienes, such as 1,3-cyclopentadiene, 1,4-cyclohexadiene, 1,5-cyclooctadiene and 1,5-cyclododecadiene;

multi-ring alicyclic fused and bridged ring dienes, such as tetrahydroindene, methyl tetrahydroindene, dicyclopentadiene, bicyclo-(2,2,1)-hepta-2,5-diene; and alkenyl, alkylidene, cycloalkenyl and cycloalkylidene norbornenes, such as 5-methylene-2-norbornene (MNB), 5-propenyl-2-norbornene, 5-isopropylidene-2-norbornene, 5-(4-cyclopentenyl)-2-norbornene, 5-cyclohexylidene-2-norbornene, 5-vinyl-2-norbornene and norbornadiene.

Preferred dienes are 1,4-hexadiene (HD), 5-ethylidene-2-norbornene (ENB), 5-vinylidene-2-norbornene (VNB), 5-methylene-2-norbornene (MNB) and dicyclopentadiene (DCPD). Particularly preferred dienes are 5-ethylidene-2-norbornene (ENB) and 1,4-hexadiene (HD).

When present the non-conjugated dienes are preferably incorporated into the polymer in an amount from 0.1% to about 20% by mol, preferably from 0.5% to 15% by mol, and more preferably from 0.5% to 7% by mol. If desired, more than one diene may be incorporated simultaneously, for example HD and ENB, with total diene incorporation within the limits specified above.

The processes of the present invention can be carried out in one reactor or in two or more reactors in series.

Further object of the present invention is a ligand of formula (III)

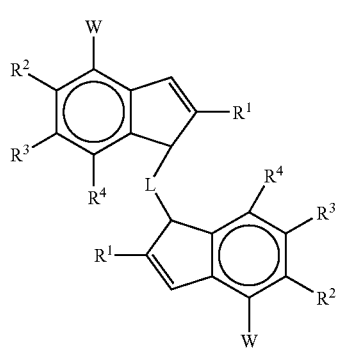

(III)

or its double bond isomers wherein L, $R^1$, $R^2$, $R^3$, $R^4$, and W have the meaning reported above Preferred ligand has formula (IIIa):

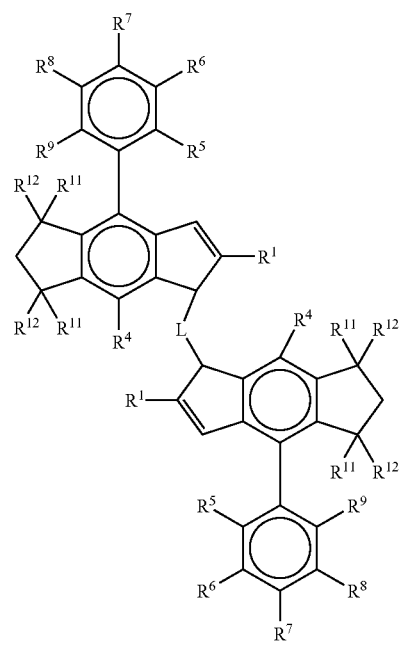

(IIIa)

or its double bond isomers wherein L, $R^1$, $R^4$, $R^5$, $R^6$, $R^7$, $R^8$, $R^9$, $R^{11}$ and $R^{12}$ have the meaning reported above.

A further preferred ligand has formula (IIIb)

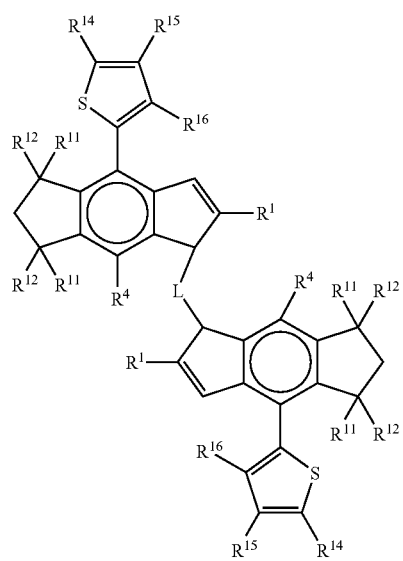

(IIIb)

or its double bond isomers wherein L, $R^1$, $R^4$, $R^{14}$, $R^{15}$, $R^{16}$, $R^{11}$ and $R^{12}$ have the meaning reported above.

The metallocene compounds of formula (I) can be obtained with a process comprising the steps of reacting the dianion with a suitable transition metal source such as metal tetrahalide as for example zirconium tetrachloride. The dianion can be obtained for example by the deprotonation of the ligand of formula (III), for example by using an organolithium compound such as buthyl or methyl lithium.

The ligand of formula (III) can be easily prepared starting from the cyclopentadienyl moiety of formula (IV)

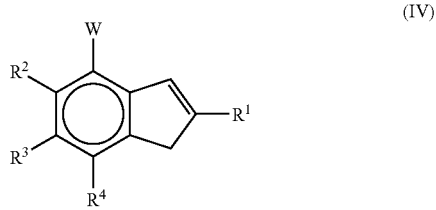

wherein $R^1$, $R^2$, $R^3$, $R^4$ and W have the meaning described above with a process comprising the following steps:

a) Contacting the compound of formula (IV) and/or its double bond isomers with a base selected from $T_jB$, $TMgT^1$, sodium and potassium hydride, metallic sodium and potassium; wherein T, j, B and $T^1$ are defined as above, and wherein the molar ratio between said base and the compound of the formula (IV) is at least 1:1; excess of said base can be used;

b) contacting the anionic compound obtained in step a) with a compound of formula $LY^2$ wherein L is defined as above and Y is chlorine, bromine and iodine, preferably Y is chlorine or bromine; to form a compound of formula (IVa)

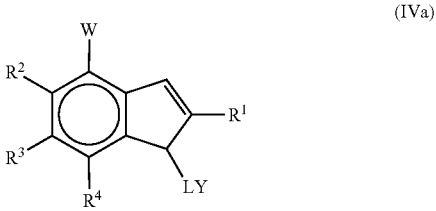

c) contacting the compound of formula (IVa) with the anionic derivative of compound of formula (IV) obtained as described in step a).

The process described above can be carried out also "one pot" by reacting a calculate amount of the compound of formula $LY_2$ with the dianionic derivative formed in step a). The above processes are preferably carried out in an aprotic solvent, either polar or apolar. Said aprotic solvent is preferably an aromatic or aliphatic hydrocarbon, optionally halogenated, or an ether; more preferably it is selected from benzene, toluene, pentane, hexane, heptane, cyclohexane, dichloromethane, diethylether, tetrahydrofurane and mixtures thereof. The above process is carried out at a temperature ranging from −100° C. to +80° C., more preferably from −20° C. to +70° C.

The following examples are given to illustrate and not to limit the invention.

EXAMPLES

General Characterization

Intrinsic viscosity (IV) in Decahydronaphthalene

The intrinsic viscosity in Decahydronaphthalene (DHN) was determined on an Ubbelohde viscometer PVS 1 with an S 5 measuring head (both from Lauda) in decalin at 135° C. To prepare the sample, 20 mg of polymer were dissolved in 20 ml of decalin at 135° C. over a period of 2 hours. 15 ml of the solution were placed in the viscometer; the instrument carried out a minimum of three running-out time measurements until a consistent result had been obtained. The IV was calculated from the running-out times according to IV=(t/t0−1)*1/c where t: mean of the running-out time of the solution, t0: mean of the running-out time of the solvent, c: concentration of the solution in g/ml.

Intrinsic Viscosity (IV) in Tetrahydronaphthalene

The measurement for examples 1-5 were done in tetrahydronaphthalene (THN) solution obtained by dissolving the polymer at 135° C. for 1 hour as described above.

Xylene Soluble Fraction at 25° C.

2.5 g of polymer were dissolved in 250 ml of o-xylene under stirring at 135° C. for 30 minutes, then the solution was cooled to 25° C. and after 30 minutes the insoluble polymer was filtered. The resulting solution was evaporated in nitrogen flow and the residue was dried and weighed to determine the percentage of soluble polymer.

Melting Temperature Tm

Calorimetric measurements were performed by using a differential scanning calorimeter DSC Mettler. The instrument is calibrated with indium and tin standards. The weighted sample (5-10 mg), was sealed into aluminum pans, heated to 200° C. and kept at that temperature for a time long enough (5 minutes) to allow a complete melting of all the crystallites. Successively, after cooling at 20° C./min to 0° C. and standing for 5 minutes at 0° C., the sample was heated to 200° C. at a rate of 20° C./min. In this second heating run, the peak temperature was assumed as melting temperature ($T_m$) and the area as the global melting enthalpy (ΔH).

Gel Permeation Chromatography

Gel permeation chromatography (GPC) was carried out at 145° C. in 1,2,4-trichlorobenzene using a GPC apparatus 150C from Waters. The data were evaluated using the software Win-GPC from HS-Entwicklungsgesellschaft fürwissenschaftliche Hard-und Software mbH, Ober-Hilbersheim. The calibration of the columns was carried out by means of polypropylene standards having molar masses of from 100 to 107 g/mol. Mass average molar masses (Mw) and number average molar masses (Mn) of the polymers were determined.

Chemicals and Characterization.

All chemicals were handled using standard Schlenk techniques.

Methylalumoxane (MAO) was received from Albemarle as a 30% wt/V toluene solution and used as such and the silica was received from INEOS (ES70Y, 100 microns).

Synthesis of rac-μ-{bis-[η⁵-2-methyl-4-(4-tert-butylphenyl)-1,5,6,7-tetrahydro-s-indacen-1-yl]dimethylsilanediyl}dichlorozirconium (IV) (A-1)

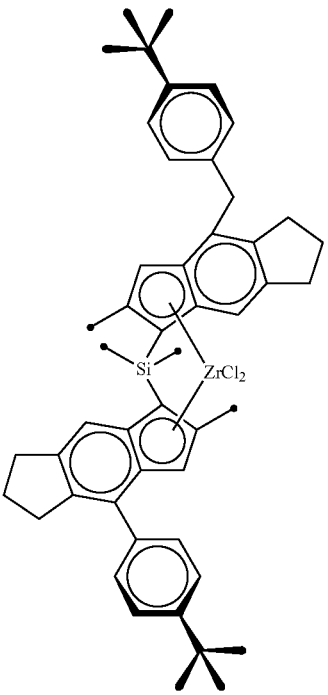

a) Synthesis of Dimethyl[bis(2-methyl-4-(4-tert-butylphenyl)-1,5,6,7-tetrahydro-s-indacen-1-yl)]silane Solution of 6-methyl-4-(4-tert-butylphenyl)-1,2,3,5-tetrahydro-s-indacene prepared as described in PCT/EP2004/013827 (4.06 g, 13.4 mmole) in Et$_2$O (50 ml)) was cooled to −40° C., and n-BuLi in hexane (1.6M, 8.57 ml, 13.7 mmole) was added. Resulting mixture was allowed to warm to room temperature, stirred for 2 h, cooled to −60° C., and CuCN (74 mg, 0.8 mmole) was added. After 15 min SiMe$_2$Cl$_2$ (0.81 ml, 6.71 mmole) was added. Resulting mixture was allowed to warm to room temperature, stirred for 16 h. H$_2$O (5 ml) and hexane (200 ml) were added, organic phase was separated, dried over MgSO$_4$, passed through silica gel and evaporated. The residue was dried in vacuo. The product was used without purification.

$^1$H NMR (CDCl$_3$, 20° C.) δ: 7.60-7.30 {groups of m, 10H, Aryl}; 6.72 (bs, 2H, —CH=); 3.87 (s); 3.86 (s) {2H, >CH—}; 3.12-2.89 (m); 2.14 (m) {12H, —CH$_2$—}; 2.33 (s); 2.27 (s) {6H, C—CH$_3$}; 1.50 (s, 18H, —C(CH$_3$)$_3$); -0.10 (bs, 6H, S$_1$—CH$_3$).

b) Synthesis of μ-{bis-[η⁵-2-methyl-4-(4-tert-butylphenyl)-1,5,6,7-tetrahydro-s-indacen-1-yl]dimethylsilanediyl}dichlorozirconium (IV) (A-1)

Obtained dimethyl[bis(2-methyl-4-(4-tert-butylphenyl)-1,5,6,7-tetrahydro-s-indacen-1-yl)]silane (4.65 g, 7.03 mmole) was dissolved in Et$_2$O (40 ml), cooled to −40° C., and n-BuLi (1.6M in hexane, 9.23 ml, 14.8 mmole) was added. Reaction mixture was allowed to warm to room temperature, stirred for 3 h, and evaporated. Resulting orange-yellow powder was suspended in pentane (100 ml), cooled to −60° C., and ZrCl$_4$ (1.73 g, 7.39 mmole) was added. After 5 min Et$_2$O (1 ml) was added. Resulting mixture was allowed to warm to room temperature with stirring, stirred for additional 16 h, and filtered. Resulting orange-yellow powder was dried, DME (90 ml) and LiCl (0.2 g) were added, and resulting mixture was refluxed with stirring for 6 h. The solvent was evaporated. Recrystallization of the residue from Et$_2$O leads racemic form of metallocene. The yield 0.84 g (29%)

$^1$H NMR (CD$_2$Cl$_2$, 20° C.) δ: 7.44 (bs, 10H, Ph); 6.62 (s, 2H, —CH=); 2.98-2.70; 2.00-1.91 (group of m, 12H, —CH$_2$—); 2.19 (s, 6H, C—CH$_3$); 1.34 (s, 18H, —C(CH$_3$)$_3$); 1.30 (s, 6H, S$_1$—CH$_3$).

rac-dimethylsilylbis(2-methyl-4-(para-tert-butylphenyl)-indenyl)-zirconium dichloride (rac-Me$_2$Si(2-Me-4(4tBuPh)Ind)$_2$ZrCl$_2$) (C-1)

rac-dimethylsilylbis(2-methyl-4-(para-tert-butylphenyl)-indenyl)-zirconium dichloride (rac-Me$_2$Si(2-Me-4(4tBuPh)Ind)$_2$ZrCl$_2$) (C-1) was prepared according to WO 98/40331 (example 65).

Preparation of Supported Catalyst System 6.3 g SiO$_2$ are placed in a round flask equipped with a KPG stirrer and suspended at 0° C. in 30 ml toluene. Via a dropping funnel 15.1 ml MAO are slowly added at 0° C. After addition, the suspension is allowed to come to room temperature (RT), and is then stirred for 2 h. The reaction mixture is placed in a stirred glass flask equipped with filter (size P3), where the solvent is filtered off. The residual is suspended in 20 ml toluene, stirred for 15 min at room temperature, and filtered. The support is suspended in 20 ml toluene, then brought to 80° C., and stirred for 30 min at this temperature before hot filtration. Again, the support is suspended in 20 ml toluene, then brought to 80° C., and stirred for 30 min at this temperature before hot filtration. The MAO/silica is suspended at 15° C. in 20 ml toluene. Under stirring, a solution of 0.25 mmol (207 mg, 40 µmol/g carrier) of the metallocene indicated in table 1 in 2 ml MAO and 2 ml toluene is slowly added. The reaction mixture is stirred for 1 h at 15° C., and after raising the temperature to 40° C., again stirred for 2 h. Then, it is filtered. The residual solid is washed 3 times at 60° C. with 20 ml toluene each (stirring: 3×30 min). After the last filtration, the reaction product is transferred with some toluene into a glass frit (size P3), and filtered again. The catalyst is transfer after drying at RT in high vacuum until weight constant.

Polymerization Examples 1-2

Multistep Polymerization

Step a)

A 2.5 L autoclave, previously kept overnight under nitrogen purge, is added with 2 mmol Triethylaluminum (TEA) (as 10% w/v hexane solution) as reactor scavenger. Also 0.5 bar-g of propylene are fed to prevent air insertion in the reactor.

Prepolymerization: 252 g propylene are fed in the autoclave at 0° C. The catalytic system is injected in the reactor and propylene is prepolymerized at 30° C. for 5 minutes. At the end of this step the reactor temperature was raised from 30 to 70° C. (in 10 minutes). During the temperature increase also 59 cc H$_2$ are fed, corresponding to 2.63 mmol H$_2$. Propylene polymerization in bulk this step is carried out at 30 bar -g pressure and 70° C. until the liquid propylene is totally consumed, and the pressure inside the reactor starts to decrease. When this step is completed, the PP matrix polymerization time is recorded and the pressure is released down to 0.1 bar-g propylene; at the same time the temperature decreases to 30° C.

Step b)

Ethylene and propylene at a molar ratio ethylene(C2)/propylene(C3)+ethylene(C2) of 0.3 are feed in the reactor to reach the pressure of 21 bar-g then the temperature is raised to 60° C. and the ethylene/propylene mixture is feed at constant pressure until 232 g of monomers are consumed.

Then the reactor is vented and cooled down to room temperature; thus, the reaction is stopped. The polymer is collected and dried at reduced pressure and 60° C.

The resulting polymer has been subjected to xylene extraction at 25° C. according to the procedure described above. The fraction of polymer soluble in xylene at 25° C. has been taken as the amount of ethylene propylene copolymers produced in the process. The polymerization data are reported in table 1

TABLE 1

| Ex | Met | Step a) Activity Kg PP/g catalyst/ hour | Step b) Activity Kg EPR/g catalyst/ hour | $C2_{EPR}$ % wt | X.S. % wt | IV xs dl/g THN | Tm C. ° |
|---|---|---|---|---|---|---|---|
| 1 | A-1 | 4.4 | 6.4 | 26.3 | 70.7 | 2.55 | 153.2 |
| 2* | C-1 | 2.5 | 2.3 | 21.0 | 65.9 | 0.71 | 152.0 |

*comparative

EPR Propylene Ethylene Polymer

Activities are referred to the catalyst as a whole, i.e. metallocene+MAO+Silica

Polymerization Example 4

Multistep Polymerization

Step a)

A 2.5 L autoclave, previously kept overnight under nitrogen purge, is added with 2 mmol Triethylaluminum (TEA) (as 10% w/v hexane solution) as reactor scavenger. Also 0.5 bar-g of propylene are fed to prevent air insertion in the reactor.

Prepolymerization: 134 g propylene are fed in the autoclave at 0° C. The catalytic system is injected in the reactor and propylene is prepolymerized at 30° C. for 5 minutes. At the end of this step the reactor temperature was raised from 30 to 80° C. (in 10 minutes). Propylene polymerization in gas phase: this step is carried out at 21 bar-g pressure and 80° C. until 70 grams of propylene are consumed and the pressure inside the reactor starts to decrease. When this step is completed, the PP matrix polymerization time is recorded and the pressure is released down to 0.1 bar-g propylene; at the same time the temperature decreases to 30° C.

Step b) In examples 4-6 the procedure used in examples 1-3 has been repeated excepting that the Ethylene propylene molar ratio (ethylene(C2)/propylene(C3)+ethylene(C2)) fed was 0.2 and the polymerization in step b) was stopped when 232 grams of monomers were consumed. The results are reported in table 2

TABLE 2

| Ex | Met | Step a) Activity Kg PP/g catalyst/ hour | Step b) Activity Kg EPR/g catalyst/ hour | $C2_{EPR}$ % wt | X.S. % wt | IV xs THN | Tm C. ° |
|---|---|---|---|---|---|---|---|
| 4 | A-1 | 0.5 | 3.6 | 14.2 | 79 | 2.83 | 154 |

* comparative

EPR Propylene Ethylene Polymer

From table 1 clearly results that the polymerization activity of the catalyst system based on the metallocene compound of the present invention show an activity higher than the metallocene compound having the closest structure, both in propylene polymerization and propylene/ethylene copolymerization. Moreover the molecular weight of the propylene copolymer obtained with the metallocene of the present invention is considerably higher.

Example 6

Propylene Homopolymerization

Preparation of the Catalyst System 0.206 mmol of a metallocene dichloride (A-1) were added at room temperature to 4.33 mmol of MAO (30% strength solution in toluene, from Albemarle). The solution was allowed to stand overnight at room temperature and was subsequently diluted with 10.9 ml of toluene. The diluted solution was carefully added to 10 g of silica (Sylopol 948, calcined at 600° C., from Grace). Particular attention was paid to the colored solution being uniformly distributed over the support material. After 10 minutes, the flask containing the catalyst suspension was connected to a vacuum line and dried until the content of volatile material had been reduced to less than 5% by weight.

Propylene Homopolymerization

Homopolymerizations were carried out in a 10 l reactor charged with 3.5 kg of liquid propene. The reactor was made inert by means of nitrogen before being charged. 8 ml of a 20% strength by weight solution of triethylaluminum in Exxsol (from Witco) were introduced into the reactor and the mixture was stirred at 30° C. for 15 minutes. A suspension of the respective catalyst as indicated in table 3 in 20 ml of Exxsol was introduced into the reactor. The reactor temperature was increased to 65° C. and maintained at this temperature for 60 minutes. The polymerizations were stopped by venting the reactor. The polymers were dried overnight under reduced pressure before being analyzed.

The polymerization results are reported in table 3

TABLE 3

| Ex | Met. | Cat amount (mg) | Activity (kg/g-cat · h) | Mw ($10^3$ g/mol) | Mw/Mn | Tm ° C. | X.S. % |
|---|---|---|---|---|---|---|---|
| 6 | A-1 | 608 | 1.7 | 1200 | 3.9 | 153.4 | 0.06 |

Polymerization Examples 7-13

Propylene/Ethylene Copolymerization

Step a)

A 11.7 L autoclave, previously kept overnight under nitrogen purge, is added with 8 mmol Triisobutylaluminum (TIBA) (as 20% wt/wt in Exxsol, 0.77 mol/L) as reactor scavenger. The autoclave is filled with 550 g Propylene and 70 mg Hydrogen.

Still at room temperature the catalytic system obtained as described above (the metallocene used is A-1 amounts indicated in table 4) is injected in the reactor by using additional 150 g liquid propylene.

The temperature is increased at 40° C., in 2-3 minutes, and the propylene is polymerized at this temperature for 5 minutes.

Step b)

At the end of the prepolymerization step the monomer is totally flashed out. The reactor is filled with the fresh Ethylene/Propylene monomer mixture and the temperature is increased to 60° C. in order to reach the desired polymerization pressure (21 barg). This step needs about 10 minutes.

Step c)

The ethylene/propylene mixture is fed at constant pressure for 60 minutes. Then the reactor is vented and cooled down to room temperature; thus, the reaction is stopped. The polymer is collected and dried at reduced pressure and 60° C.

The resulting polymer has been subjected to xylene extraction at 25° C. according to the procedure described above. The fraction of polymer soluble in xylene at 25° C. has been taken as the amount of ethylene propylene copolymers produced in the process. The polymerization data are reported in table 4

TABLE 4

| Ex. | A-1 mg | Al/Zr Molar ratio | C3- fed [g] | C2% wt fed | Activity [kg/g Zr/h] | C2-% wt | I.V. dL/g |
|---|---|---|---|---|---|---|---|
| 7 | 1.1 | 285 | 703 | 45 | 5979 | 43.6 | 3.7 |
| 8 | 1.1 | 285 | 703 | 30 | 5576 | 32.0 | 3.8 |
| 9 | 1.2 | 285 | 699 | 73 | 1395 | 57.0 | 3.7 |
| 10 | 1.3 | 262 | 700 | 30 | 3311 | 21.8 | 3.7 |
| 11 | 1.0 | 262 | 698 | 61 | 2437 | 49.0 | 3.7 |
| 12 | 0.9 | 262 | 697 | 21 | 3135 | 15.3 | 3.8 |
| 13 | 0.9 | 262 | 698 | 13 | 1302 | 8.5 | 3.8 |

C3 = propylene; C2 = ethylene

In examples 7-13 it is shown that the molecular weight of the polymer does not substantially change by increasing the ethylene content.

Polymerization Examples 14-24

Propylene Polymerization in Slurry with Hydrogen

The catalyst system was prepared according to example 6 above by using A-1.

Propylene Homopolymerization

Homopolymerizations were carried out in a 10 l reactor charged with 3.5 kg of liquid propene and an hydrogen amount as indicated in table 5. The reactor was made inert by means of nitrogen before being charged. 8 ml of a 20% strength by weight solution of triethylaluminum in Exxsol (from Witco) were introduced into the reactor and the mixture was stirred at 30° C. for 15 minutes. An amount indicated in table 5 of the catalyst system in suspension of 20 ml of Exxsol was introduced into the reactor. The reactor temperature was increased to 65° C. and maintained at this temperature for 60 minutes. The polymerizations were stopped by venting the reactor. The polymers were dried overnight under reduced pressure before being analyzed.

TABLE 5

| Example | [mg] catalyst | [NL] H$_2$ | [kg/g Zr/h] Activity | [g/dl] IV THN calc |
|---|---|---|---|---|
| 14 | 78.9 | 5 | 22068 | 3 |
| 15 | 80.9 | 2.5 | 10325 | 3.7 |
| 16 | 81.9 | 1.2 | 4345 | 4.6 |
| 17 | 78.9 | 5 | 22926 | 2.3 |
| 18 | 62.6 | 7 | 17945 | 1.8 |

In table 5 it is shown that the metallocene compounds object of the present invention increase in a considerable way the activity when hydrogen is added, but at the same time the molecular weight of the polymer obtained is still at an industrial applicable level.

The invention claimed is:

1. A catalyst system for polymerizing at least one olefin, the catalyst system obtained by contacting:

a metallocene compound of formula (II):

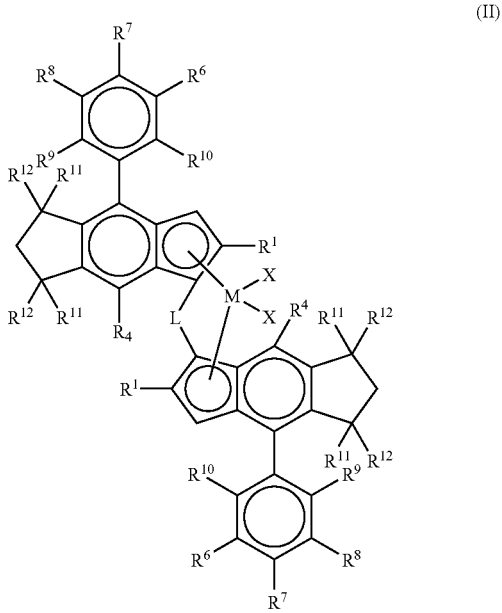

(II)

wherein

M is a Group 3 or 4 metal or a lanthanide or actinide element;

X, equal to or different from each other, is hydrogen, a halogen, R, OR, OR'O, OSO$_2$CF$_3$, OCOR, SR, NR$_2$, or PR$_2$;

R is a linear or branched, cyclic or acyclic C$_1$-C$_{40}$-alkyl, C$_2$-C$_{40}$ alkenyl, C$_2$-C$_{40}$ alkynyl, C$_6$-C$_{40}$-aryl, C$_7$-C$_{40}$-alkylaryl or C$_7$-C$_{40}$-arylalkyl, optionally comprising at least one Group 13-17 heteroatom;

R' is a C$_1$-C$_{20}$-alkylidene, C$_6$-C$_{20}$-arylidene, C$_7$-C$_{20}$-alkylarylidene, or C$_7$-C$_{20}$-arylalkylidene;

L is a divalent bridging group selected from a C$_1$-C$_{20}$ alkylidene, a C$_3$-C$_{20}$ cycloalkylidene, a C$_6$-C$_{20}$ arylidene, a C$_7$-C$_{20}$ alkylarylidene, or a C$_7$-C$_{20}$ arylalkylidene, optionally comprising at least one Group 13-17 heteroatom, or L is a silylidene radical comprising up to 5 silicon atoms;

$R^1$ is a linear $C_1$-$C_{40}$ hydrocarbon optionally comprising at least one Group 13-17 heteroatom; and each of $R^4$, $R^6$, $R^7$, $R^8$, $R^9$, $R^{10}$ $R^{11}$ and $R^{12}$ is independently hydrogen or a $C_1$-$C_{40}$ hydrocarbon, optionally comprising at least one Group 13-17 heteroatom;

at least an alumoxane or a compound capable of forming an alkylmetallocene cation; and optionally, an organo aluminum compound.

2. The catalyst system of claim 1, further comprising an inert carrier.

3. The catalyst system of claim 1, wherein $R^7$ is methyl or t-butyl.

4. A process for preparing an alpha-olefin polymer comprising, contacting under polymerization conditions, at least one alpha-olefin of formula $CH_2$=CHA, wherein A is hydrogen or a $C_1$-$C_{20}$ alkyl, in presence of the catalyst system of claim 1.

5. The process of claim 4, wherein the alpha olefin is ethylene, propylene and 1-butene.

6. The process of claim 4 wherein the alpha-olefin is propylene.

7. The process of claim 4, wherein the process is performed in the slurry or gas phase.

8. The process of claim 4, wherein $R^7$ is methyl or t-butyl.

* * * * *